(12) United States Patent  (10) Patent No.: US 10,107,749 B2
Zhang et al.  (45) Date of Patent: Oct. 23, 2018

(54) PLASMON LASER SENSOR

(71) Applicant: THE REGENTS OF THE UNIVERSITY OF CALIFORNIA, Oakland, CA (US)

(72) Inventors: Xiang Zhang, Alamo, CA (US); Ren-Min Ma, Beijing (CN); Sadao Ota, Tokyo (JP)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 32 days.

(21) Appl. No.: 15/175,670

(22) Filed: Jun. 7, 2016

(65) Prior Publication Data

US 2016/0377542 A1  Dec. 29, 2016

Related U.S. Application Data

(60) Provisional application No. 62/185,044, filed on Jun. 26, 2015.

(51) Int. Cl.
*G01N 21/55* (2014.01)
*G01N 21/552* (2014.01)
*G01N 33/00* (2006.01)

(52) U.S. Cl.
CPC ....... *G01N 21/554* (2013.01); *G01N 33/0057* (2013.01)

(58) Field of Classification Search
CPC . G01N 21/553; G01N 21/554; G01N 33/0057

USPC .................................. 356/432–448, 213–236
See application file for complete search history.

(56) References Cited

U.S. PATENT DOCUMENTS

| 2013/0148682 A1* | 6/2013 | Zhang | H01S 5/1046 372/45.01 |
| 2014/0134714 A1* | 5/2014 | Valsesia | G01N 21/554 435/288.7 |
| 2014/0353577 A1* | 12/2014 | Agarwal | C09K 11/565 257/10 |

OTHER PUBLICATIONS

Ma, Ren-Min et al., "Explosives detection in a lasing plasmon nanocavity", Nature Nanotechnology, published online at http://www.nature.com/doifinder/10.1038/nnano.2014.135, Jul. 20, 2014, pp. 1-5.

* cited by examiner

*Primary Examiner* — Tri T Ton
(74) *Attorney, Agent, or Firm* — O'Banion & Ritchey LLP; John P. O'Banion (57) ABSTRACT

An active plasmon sensor comprising a single crystalline semiconductor CdS nano-slab atop a silver surface separated by a magnesium fluoride ($MgF_2$) gap layer. The surface plasmon effect localizes the electromagnetic field at the interface between the metal and semiconductor, allowing both the device's physical size and mode confinement to shrink down to the nanometer scale in a dimension perpendicular to the metal surface.

12 Claims, 9 Drawing Sheets

PLASMON LASER SENSOR

CROSS-REFERENCE TO RELATED APPLICATIONS

This application claims priority to, and the benefit of, U.S. provisional patent application Ser. No. 62/185,044 filed on Jun. 26, 2015, incorporated herein by reference in its entirety.

STATEMENT REGARDING FEDERALLY SPONSORED RESEARCH OR DEVELOPMENT

This invention was made with Government support under FA9550-12-1-0197, awarded by the Air Force Office of Scientific Research (AFOSR). The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to sensors, and more particularly to a plasmon laser sensor.

2. Background Discussion

One particularly beneficial application of plasmonics thus far has been in the field of sensing, where the interaction of a nanoscale localized field with analytes leads to high sensitive detection in real-time and label-free fashion. However, previous designs have been based on passively excited surface plasmons (SPs), in which sensitivity is intrinsically limited by low quality factors induced by metal losses.

While cavities in which the light-matter interaction is greatly enhanced provide a promising platform for sensing, the sensitivity of these detectors is ultimately determined by the quality factor of the cavity modes and the surface to volume ratio, and the diffraction limit of light creates a hurdle to improve these two features simultaneously in a conventional optical cavity. Surface plasmons (SP) are able to achieve nanoscale confinement of electromagnetic fields, but existing SP sensors are passively excited and suffer from the intrinsically high ohmic losses in metals, resulting in low quality factor of the resonances and thus limiting its sensitivity.

Accordingly, an object of the present description is an SP sensor with active (gain enhanced) excitations that exhibit well-confined strong local fields, increased radiating power, and dramatically narrowed line-width for achieving higher sensitivities due to the amplification of the SPs.

BRIEF SUMMARY

An aspect of the present description is an active plasmon sensor, free of metal losses and operating deep below the diffraction limit for visible light. Loss compensation leads to an intense and sharp lasing emission that is ultra-sensitive to adsorbed molecules.

In one embodiment, the device of the present description comprises a single crystalline semiconductor CdS nano-slab (50 nm in thickness, 600 nm in length) atop a silver surface separated by an 8 nm thick magnesium fluoride ($MgF_2$) gap layer. The surface plasmon (SP) effect localizes the electromagnetic field at the interface between the metal and semiconductor, allowing both the device's physical size and mode confinement to shrink down to the nanometer scale in a dimension perpendicular to the metal surface. The semiconductor slab comprises an atomically smooth surface simultaneously that serves as the gain and nanoscale sensing medium in the lasing plasmon nano-cavity. The large surface to physical volume ratio ($S/V_{phy}$) of the nano-cavity, which is inversely proportional to the nano-slab thickness, strengthens the surface modulation effect to the emission. While the large surface area (S) favors the analytes' adsorption, the small physical volume of active material $V_{phy}$ limits the number of carriers to be modulated inside. In the device of the present description, the estimated number of carriers for the plasmon lasing operation is only about $2\times10^4$, making the emission intensity intrinsically sensitive to a highly limited number of surface events.

The efficacy of the sensor was verified for detection of explosives in air under normal conditions and was shown to achieve a sub-ppb detection limit, the lowest limit reported so far for plasmonic sensors, for 2, 4-dinitrotoluene (DNT) and ammonium nitrate (AN). Selectivity between DNT, AN and nitrobenzene (NB) is on-par with other state-of-the art explosive detectors. Furthermore, results show that monitoring the change of the lasing intensity is a method with superior performance than monitoring the wavelength shift, which is widely used in passive surface plasmon sensors.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 8A through FIG. 8C illustrate detection of explosive molecules via spontaneous emission.

DETAILED DESCRIPTION

Figure 1:
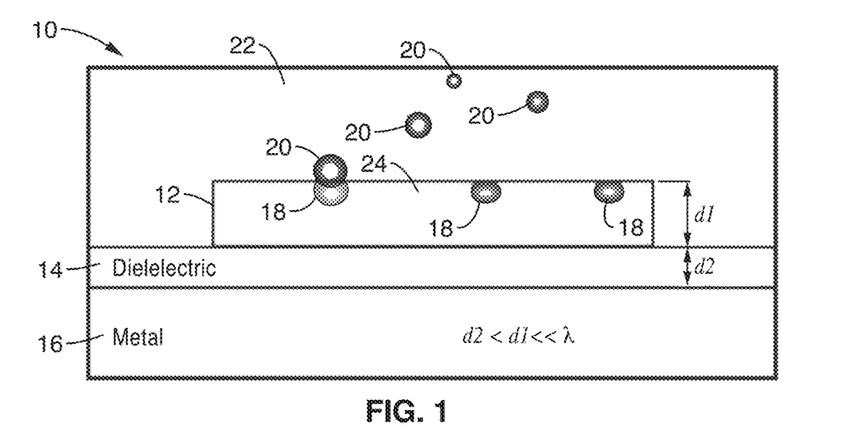
FIG. 1 is a schematic diagram of an active plasmon nanosensor in accordance with the present description.
Figure 2A:
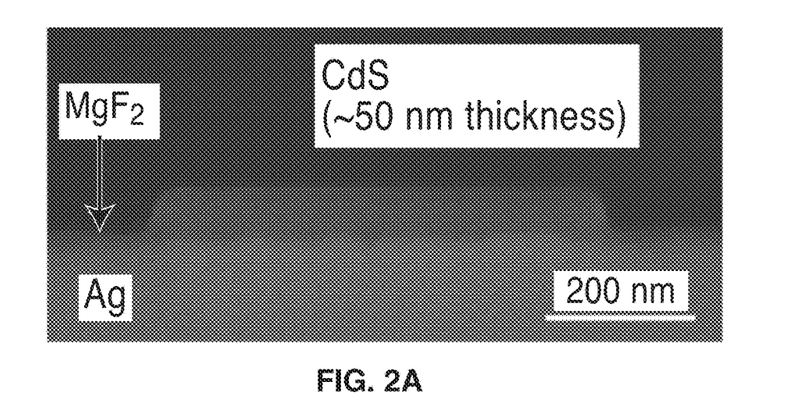
FIG. 2A shows an SEM image of an active plasmon nanosensor similar to that of FIG. 1, comprising a CdS nano-slab with thickness of 50 nm and length of 600 nm atop silver film separated by an 8 nm low-permittivity $MgF_2$ layer.

FIG. 1 is a schematic diagram of an active plasmon nanosensor 10 in accordance with the present description. FIG. 2A shows an SEM image of an active plasmon nanosensor similar to that of FIG. 1.

The sensor may comprise a layer of crystalline semiconductor material, a layer of a metallic material, and a layer of dielectric material between the layer of crystalline semiconductor material and the layer of metallic material. By way of example, and not of limitation, in one embodiment illustrated in FIG. 1, the nanosensor 10 comprises a single-crystalline semiconductor nano-slab 12 disposed atop a metallic surface 16 separated by dielectric gap layer 14.

In a preferred embodiment, the single-crystalline semiconductor nano-slab layer 12 comprises a CdS layer having a thickness d1 of approximately 50 nm and a length of approximately 600 nm. While CdS is a preferred composition for the nano-slab layer 12, it is appreciated that other semiconductors may also be implemented, such as, but not limited to, ZnO, CdS, CdTe, GaAs, InP, GaN, InGaN, InGaAsP. Additionally, the thickness d1 may range from approximately 10 nm to approximately 1000 nm.

In a preferred configuration, the gap layer 14 comprises a layer of magnesium fluoride ($MgF_2$) that has a thickness d2 of 8 nm. While $MgF_2$ is a preferred composition for the gap layer 14, it is appreciated that other dielectric materials may also be implemented, such as, but not limited to, LiF, $SiO_2$, $Al_2O_3$ and self-assembled polymer. Additionally, the thickness d2 may range from approximately 1 nm to approximately 50 nm.

The metallic layer 16 comprises silver in a preferred configuration. It is appreciated that other metals may also be implemented, such as, but not limited to, gold, aluminum, and copper.

In a preferred embodiment, the sensing mechanism of device 10 is based on the intensity change of stimulated emission from lasing plasmon nano cavity with subwavelength electromagnetic field confinement, wherein the semiconductor slab 12 acts as optical gain as well as sensing material simultaneously. DNT (e.g., 2, 4-dinitrotoluene) molecules 20 within the cavity 22 are absorbed on the sensing surface 24 of the device 10, which then forms a surface defect 18 on the surface 24. In one sensing modality, the surface defect 18 modifies the localized charge layer at the surface 24 giving rise to an electrostatic field in the near-surface region within the semiconductor 12.

Figure 2B:
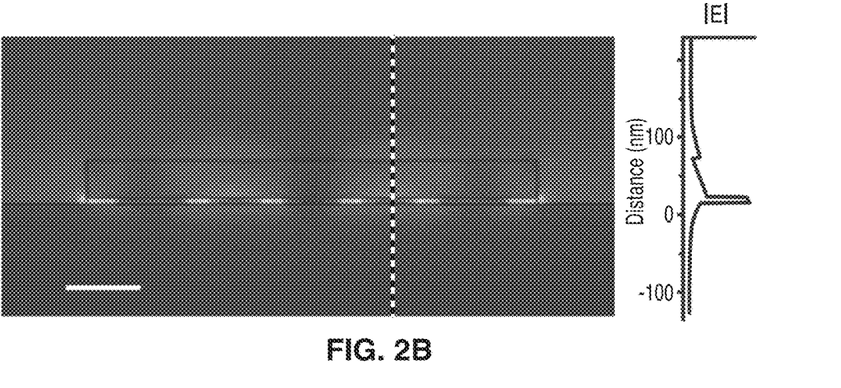
FIG. 2B shows an image of electric field distribution in a cross section of electromagnetic nano-slab cavity mode simulated in 3D space.

The SP effect localizes the electromagnetic field at the interface between the metal 16 and semiconductor 12, allowing both the device's physical size and mode confinement to shrink down to the nanometer scale in a dimension perpendicular to the metal surface 24 (see FIG. 2B). The calculated mode volume is only about 0.03 $\lambda^3$. The semiconductor slab 12 comprising an atomically smooth surface 24 (FIG. 2C) simultaneously serves as the gain and nanoscale sensing medium in the lasing plasmon nano-cavity. The large surface to physical volume ratio ($S/V_{phy}$) of the nano-cavity 22, which is inversely proportional to the nano-slab thickness, strengthens the surface modulation effect to the emission. While the large surface area S of surface 24 favors the analytes' adsorption, the small physical volume $V_{phy}$ limits the number of carriers to be modulated inside. In the device 10 of the present description, the estimated number of carriers for the plasmon lasing operation is only about $2 \times 10^4$, making the emission intensity intrinsically sensitive to a highly limited number of surface events.

Figure 3:
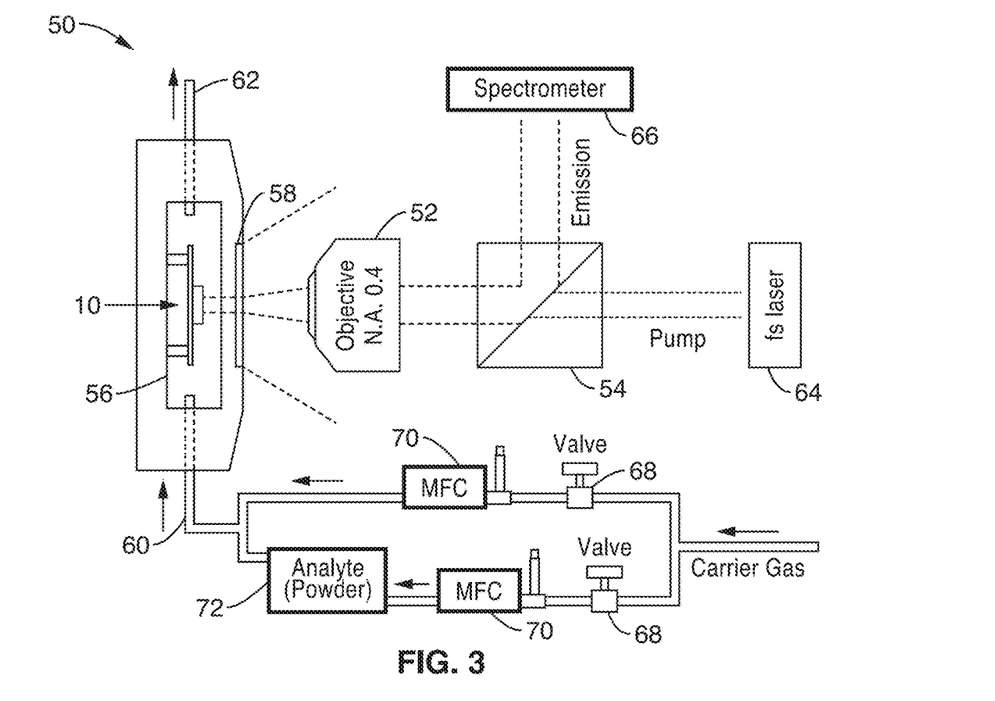
FIG. 3 shows a schematic diagram of an experimental setup for characterization of the active plasmon sensor 10 of the present description. The device is placed in a sealed chamber with two ports for gas exchange controlled by mass flow controllers (MFC) and an optical window for both the pumping and signal collection.

Referring now to FIG. 3, the characterization of the device 10 sensitivity was performed in a test setup 50 comprising a sealed chamber 56 with an inlet port 60 and outlet port 62 for gas exchange and an optical window 58 coupled to objective 52 and beam splitter 54 for both the optical pumping of light from laser 64 and signal collection of emission from spectrometer 66. The device 10 was exposed to a flow of diluted target chemical 72 at a controlled concentration. DNT with a saturation concentration of about 100 p.p.b. at room temperature was chosen as a target chemical. Inert $N_2$ gas is used to dilute DNT vapors while also serving as the background reference. A pair of mass flow controllers 70 and valves 68 were used to control whether an analyte 72 dispersed concentration or pure carrier gas (e.g. $N_2$) is delivered to the device 10. The device 10 was optically pumped above the lasing threshold at room temperature.

Figure 2C:
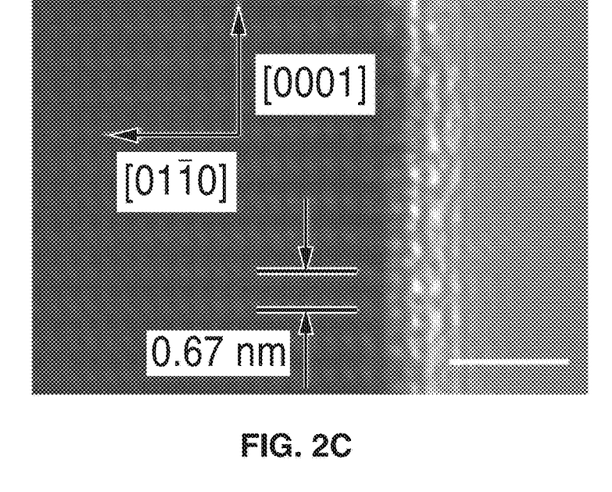
FIG. 2C shows a high resolution TEM image from a top view of CdS slab, illustrating the single crystal structure and atomic level smooth surface, along with the electric field amplitude |E| distribution along the dashed white line in left panel.

In one embodiment, the CdS nano-slabs were synthesized via a CVD method. CdS (99.995%) powders were used as the source, and pieces of Si wafers covered with 10 nm thick thermally evaporated gold catalysts were used as the substrates. The as grown CdS nano-slabs have a single crystalline lattice structure with a lattice spacing of $a_{CdS}$=0.67 nm along the [0001] axis corresponding to a wurzite crystal lattice (FIG. 2C). The silver/magnesium fluoride substrates were deposited by electron beam evaporation. The film roughness (RMS) measured by AFM is about 1 nm. CdS nano-slabs were deposited from solution by spin coating onto silver/magnesium fluoride substrates.

The active plasmon nanosensors 10 were placed in the sealed chamber 58. The saturated DNT vapor in $N_2$ is diluted by another $N_2$ channel, and thus its final concentration can be determined by the ratio of the flow rates in these two channels. The devices 10 were optically pumped by a frequency-doubled, mode-locked Ti-sapphire laser 64 (Spectra Physics) with $\lambda_{pump}$=405 nm, a 10 KHz repetition rate and approximately 100 fs pulse length. A 20× objective lens 52 (NA=0.4) was used to focus the pump beam to a ~2 μm diameter spot onto the sample 10 and collect the luminescence. All experiments were conducted at room temperature.

The optical modes of the active plasmon sensors were calculated using a finite-element method 3D eigenmode solver (Comsol Multiphysics). In this model, the CdS nano-slab ($n_{CdS}$=2.5) lies in contact with a 8 nm $MgF_2$ ($n_{MgF2}$=1.38) gap layer above a single Ag strip according to Eq. 1:

$$(\varepsilon_{Ag}=\varepsilon_b-E_p^2[E(E-i\gamma)]^{-1}, \quad \text{Eq. 1}$$

where $\varepsilon_b$=5, eV, γ=0.04 eV).

The effective mode volume of the lasing plasmon cavity is calculated as:

$$V_{eff} = \frac{\int w_{em}(\vec{r})d^3\vec{r}}{\varepsilon_0\varepsilon(|\vec{E}|_{max}^2)}, \quad \text{Eq. 2}$$

where $w_{em}$ is the electromagnetic energy density of the mode. $\vec{E}$ in the denominator is the evaluated maximal electric field.

Taking into account the strongly dispersive property of silver, $$w_{em}(\vec{r}) = \frac{1}{2}\left[\text{Re}\left[\frac{d(\omega\varepsilon)}{d\omega}\right]|\vec{E}(\vec{r})|^2 + \mu|\vec{H}(\vec{r})|^2\right]. \quad \text{Eq. 3}$$

The Q factors of the cavity modes are calculated from the formula Q=$f_r$/Δf, where the $f_r$ is the resonance frequency and Δf is the full width at half maximum of the resonance spectrum. For the Q factors of the cavity modes with introduced gain, a complex refractive index of $n_{CdS}$=n−iκ is set, where the gain coefficient κ can vary depending on the pump intensity. The Q factor is significantly enhanced by orders of magnitude with the increasing gain coefficient κ and reaches maximum at a κ value of 0.19 which corresponds to a material gain (g=4πκ/λ) of ~9500 cm⁻1.

The large surface to physical volume ratio ($S/V_{phy}$) of the nano-cavity strengthens the surface modulation effect, because the number of carriers inside is basically limited by the $V_{phy}$ and there is a large surface area for analytes absorption. $S/V_{phy}$ can also be expressed as, $s \cdot n_e/N$, where $$V_{phy} = \frac{N}{n_e}.$$

$n_e$ is the carrier concentration and N is the carrier number in the cavity. The carrier density around the lasing threshold of the plasmon nano-slab cavity is on the order of $10^{18}$ cm$^{-3}$. Given the $V_{phy}$ of the CdS nano-slab is about 0.018 μm³ (~0.14 λ³), the number of carriers for the lasing operation s number N in the device is ~1.8×10⁴.

Figure 4A:
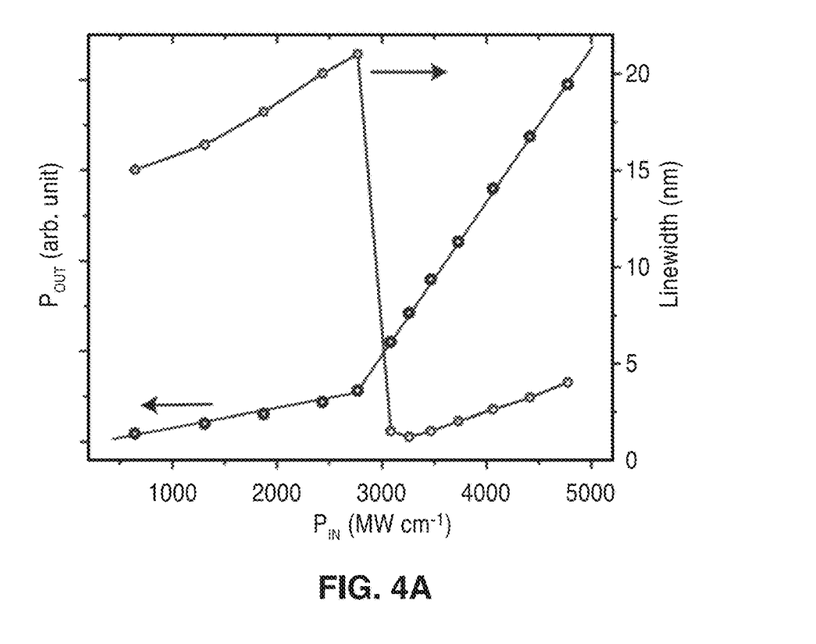
FIG. 4A is a plot showing pump intensity dependence of the total output power and line width of the device. The stimulated emission above the lasing threshold has stronger intensity, higher slope efficiency and much narrower line width than these of spontaneous emission.

FIG. 4A shows the dependence between the pump intensity and emission power and line width of the device 10. It can be seen that the lasing emission above the threshold has much narrower line width, stronger intensity and higher slope efficiency than these of spontaneous emission. These features endow the device 10 with high performance in terms of high signal intensity (I) and relative intensity change (ΔI/I) at peak wavelength.

Figure 4B:
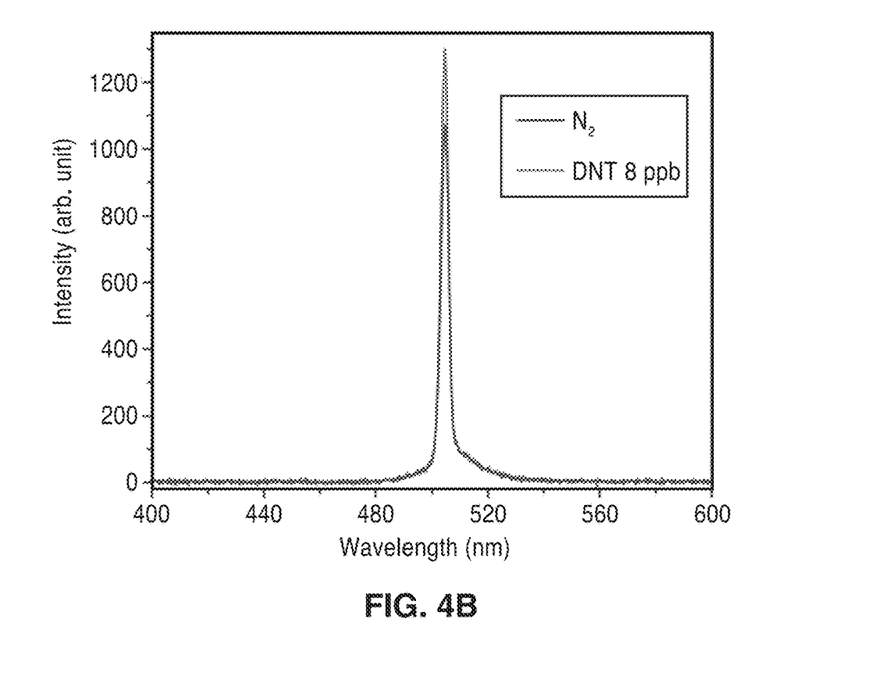
FIG. 4B is a plot of the measured spectra of the lasing plasmon cavity under $N_2$ (black curve) and 8 p.p.b. DNT (red curve).
Figure 4C:
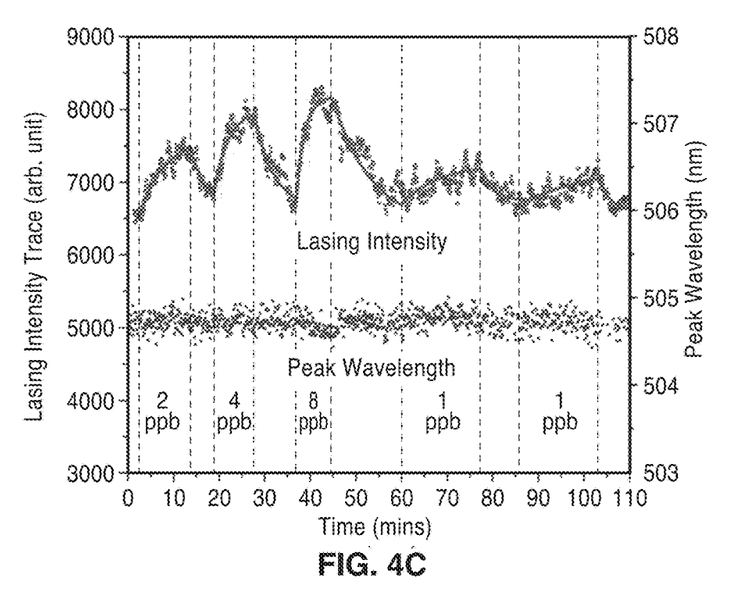
FIG. 4C is a plot of continuous trace of emission intensities (seen as small circles along line) of the active plasmon nano-sensor when delivering DNT vapors at varied concentrations of 1, 2, 4 and 8 p.p.b. The tracked lasing peak wavelength obtained by Gaussian fitting of the spectra is also plotted (shown as the lower band of dots).

In the sensing scheme of the present description, the change in the peak intensity of the lasing emission reflects the detection of molecules adsorbing on the lasing cavity. In FIG. 4B, the lasing emission spectrum under a flow of 8 p.p.b. DNT is compared with that under pure $N_2$. The surface adsorption of DNT induces an apparent change in the peak intensity at about 505 nm, while no appreciable change in the peak wavelength was observed. FIG. 4C shows the evolution of the peak intensity at 505 nm as the flow alternated between pure $N_2$ and diluted DNT at various concentrations. An increase in the peak intensity and further saturation was observed within several minutes after switching on a flow of the diluted DNT. As shown in FIG. 4C, even at the level of 1 p.p.b., a 6% of ΔI/I can be detected. The peak intensity decreased to the original value after switching back to a pure-$N_2$ flow indicating the reversible response. The response time of the device reflects a slow change of the local DNT concentration at the device surface. This transient time of about several minutes is not due to the device itself, but mainly determined by the flow rate and the volume of the chamber.

The lasing peak wavelength was also tracked via Gaussian fitting of the spectra. There is no appreciable change in the peak wavelength at various DNT concentrations (FIG. 4C dots). This observation indicates that directly monitoring the lasing intensity has superior performance compared to monitoring the index change induced peak wavelength shift in active plasmon sensors.

Figure 5:
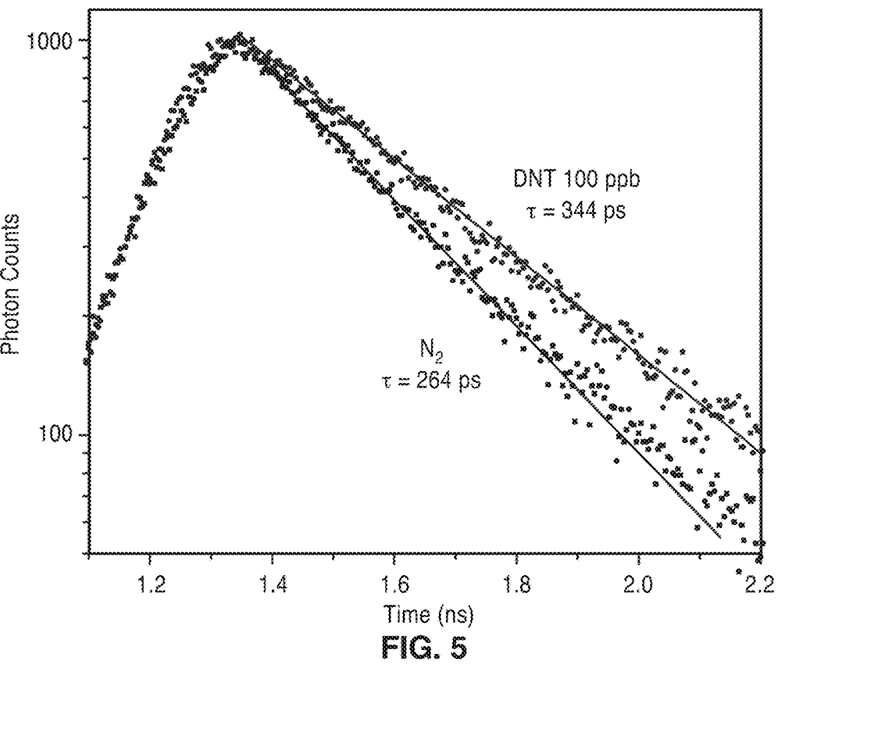
FIG. 5 is a plot of time-resolved emission of the sensor measured at the spontaneous emission region for investigating dynamic processes of the photon excited carrier relaxation. Two of the typical time-resolved spontaneous emissions under $N_2$ and 100 p.p.b. DNT are shown as the lower and upper bands, respectively.

To understand the underlying mechanism of the sensing process, the time-resolved spontaneous emission of the cavity was measured (see FIG. 5). For the intensity modification, there are two possible physical processes. The first scenario is that the absorbed DNT molecules 20 on the device modify the localized charge layer at the surface giving rise to an electrostatic field in the near-surface region within the semiconductor. The second scenario is that the DNT influences the rate of surface recombination through interactions with surface states. The former process can increase the emission intensity by mitigating the band bending, but reduce the emission lifetime because of the increased electron-hole wave function overlap. Alternatively, the adsorbed DNT can reduce the non-radiative recombination by shifting or removing the intrinsic surface state. This process increases the emission intensity and lifetime, as the total emission lifetime ($\tau$) is dependent on the radiative lifetime ($\tau_{rad}$) and non-radiative lifetime ($\tau_{nonrad}$) in the form of $$\frac{1}{\tau} = \frac{1}{\tau_{rad}} + \frac{1}{\tau_{nonrad}}.$$

In the experiment, 100 p.p.b. DNT vapor was delivered into the test setup chamber 56. The results show that the emission intensity from the device 10 increased after the introduction of the vapor, following the same trend as the stimulated emission regime. Meanwhile, the measured emission lifetime became longer as shown in FIG. 5. These results suggest that surface recombination velocity modification is preferred as the detection mechanism of the device 10.

While the detection of DNT in $N_2$ proved the principle of the sensor device 10, the path towards a practical sensor requires measuring the target molecules in air with common interferences. To achieve that, air (composed of $N_2$, $O_2$, $H_2O$, $CO_2$, CO, THC and $NO_x$ etc.) and $N_2$ were alternately delivered into the chamber. The lasing intensities increased only about 1% after each air delivery and decreased to the original value after switching back to pure $N_2$.

Figure 6A:
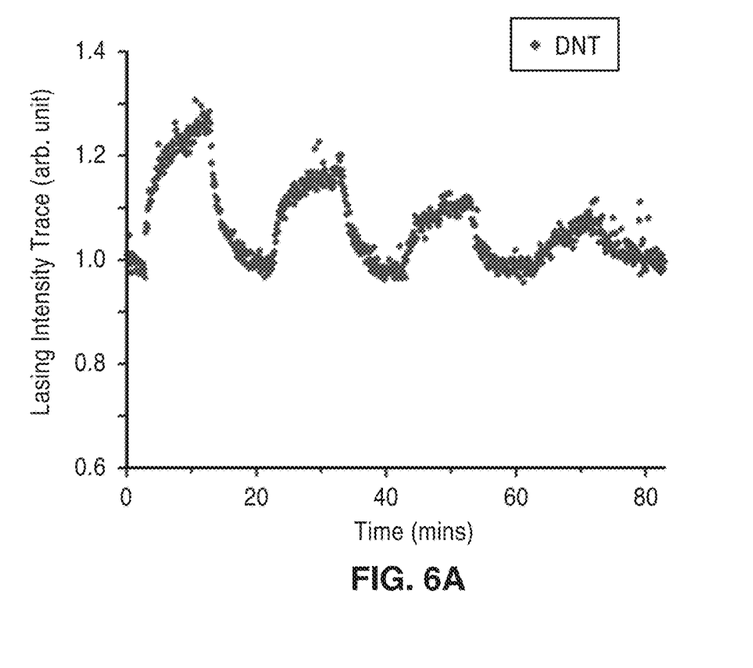
FIG. 6A through FIG. 6C show plots illustrating detection of 2, 4-dinitrotoluene (DNT), ammonium nitrate (AN) and nitrobenzene (NB) in air. Continuous traces of lasing intensities are illustrated at varied DNT (FIG. 6A), AN (FIG. 6B) and NB (FIG. 6C) vapor concentrations diluted by air.
Figure 6B:
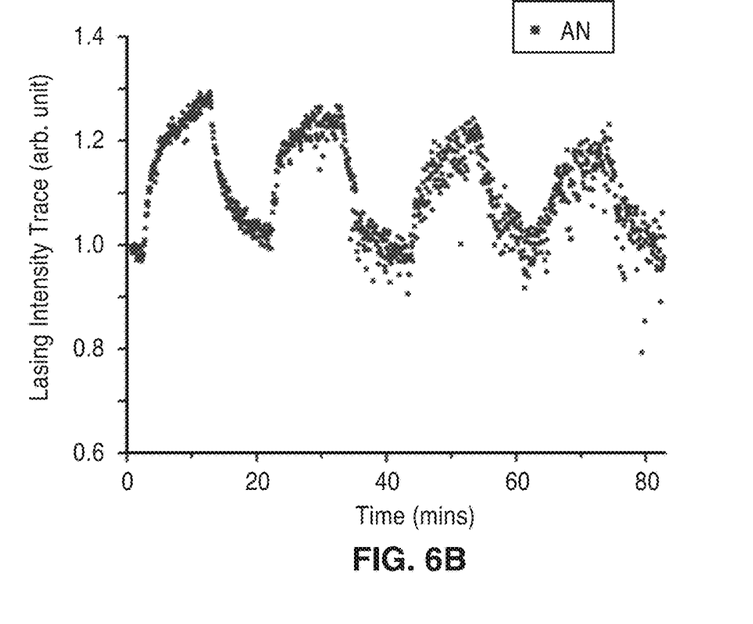
Figure 6C:
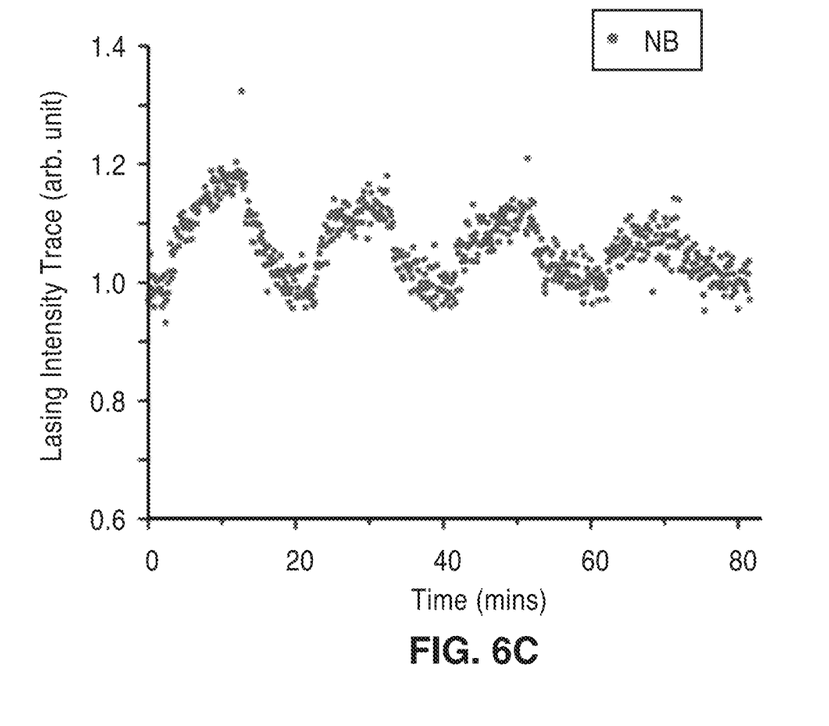
Figure 7:
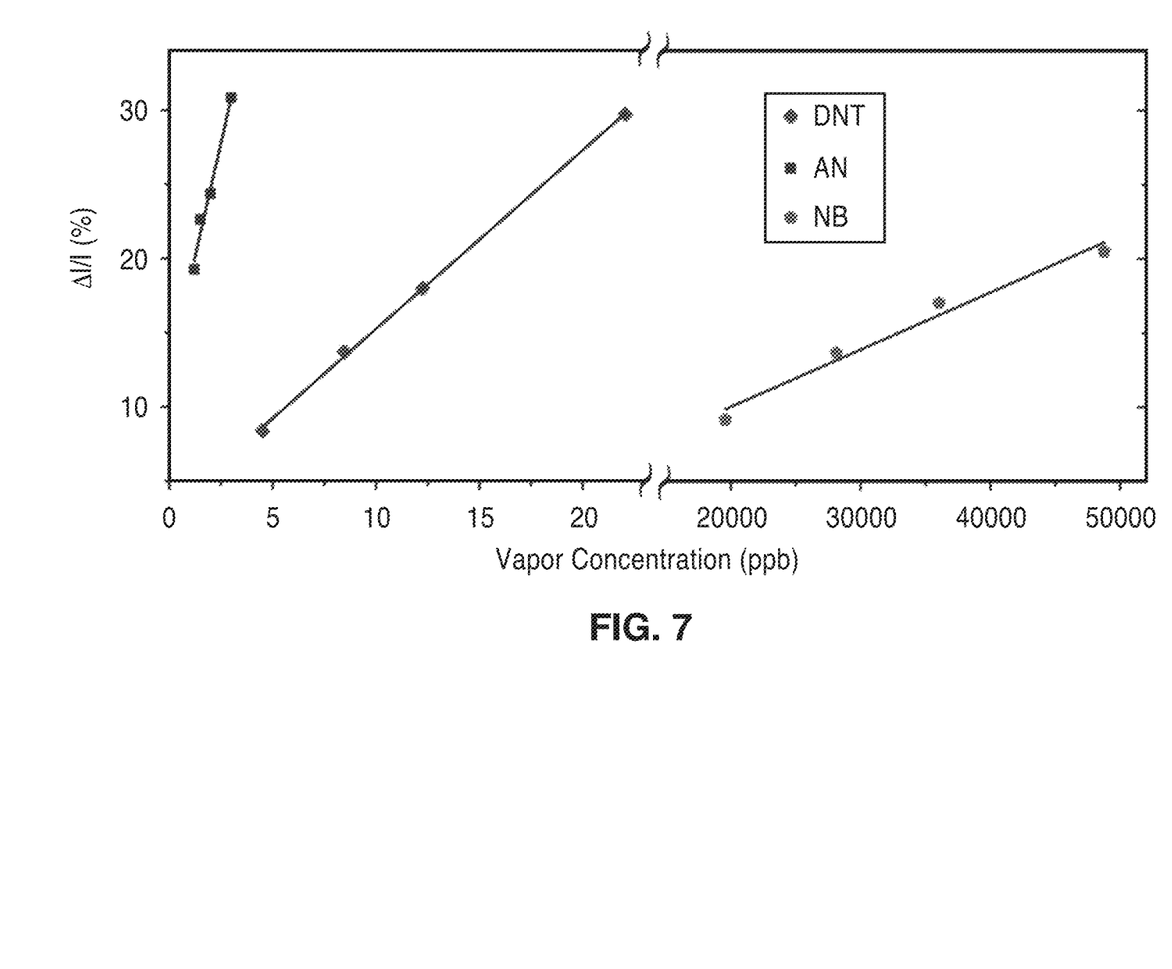
FIG. 7 illustrates calibration curves for the analytes of FIG. 6A through FIG. 6C. The sensitivities defined as the slope of the calibration curves for DNT, AN and NB are 1.2%/p.p.b., 6.1%/p.p.b. and 0.4%/p.p.m., respectively. The detection limits obtained for DNT, AN and NB are 0.67 p.p.b., 0.4 p.p.b. and 7.2 p.p.m., respectively. The device holds specific response to different target molecules due to their specific electron deficiency because our sensing is based on the surface recombination velocity modification sensitive to the electron deficiency of adsorbed molecules.

A series of experiments were then conducted to detect three different explosive molecules, DNT, AN and NB where air was used to dilute them and as the background reference. FIG. 6A through FIG. 6C show the continuous trace of lasing intensities under varied concentrations of these analytes. The lasing intensities apparently increased after each analyte delivery and decreased to the initial value after switching the input gas to only air.

The calibration curves for these three analytes were obtained from the sensor responses, where $\Delta I/I$ are plotted as a function of the analytes' vapor concentration (FIG. 6D). The sensitivities defined as the slope of the calibration curves for DNT, AN and NB are 1.2%/p.p.b., 6.1%/p.p.b. and 0.4%/p.p.m., respectively. The limits of detection of these analytes in air can also be obtained from the calibration curves. The minimum distinguishable analytical signal $S_{Iod}$ is taken as a+3S, where a and S are y-intercept and standard deviation of the regression of the calibration curves, respectively. The detection limits obtained for DNT, AN and NB are 0.67 p.p.b., 0.4 p.p.b. and 7.2 p.p.m., respectively.

Thus, it was demonstrated that the sensor 10 of the present description responds to the different analytes in air with good robustness, reversibility, as well as stability over the long lasting experiments (>5 hours). It is noted that the sensor 10 is based on the surface recombination velocity modification sensitive to the electron deficiency of adsorbed molecules. The device 10 can identify different explosive trace with distinct sensitivity when only one explosive presented in air. However, to distinguish each type of explosive in a mix of multiple explosives is still a challenging task. Nevertheless, in field applications such as airport, detecting explosives of any kind in air is sufficiently useful for the first alarm, even without distinguishing them. Use of a sensor matrix, coating with appropriate functional molecules or utilizing enhanced Raman signal in the lasing plasmon senor may be used to explore on the specific response of an analyte.

Figure 8A:
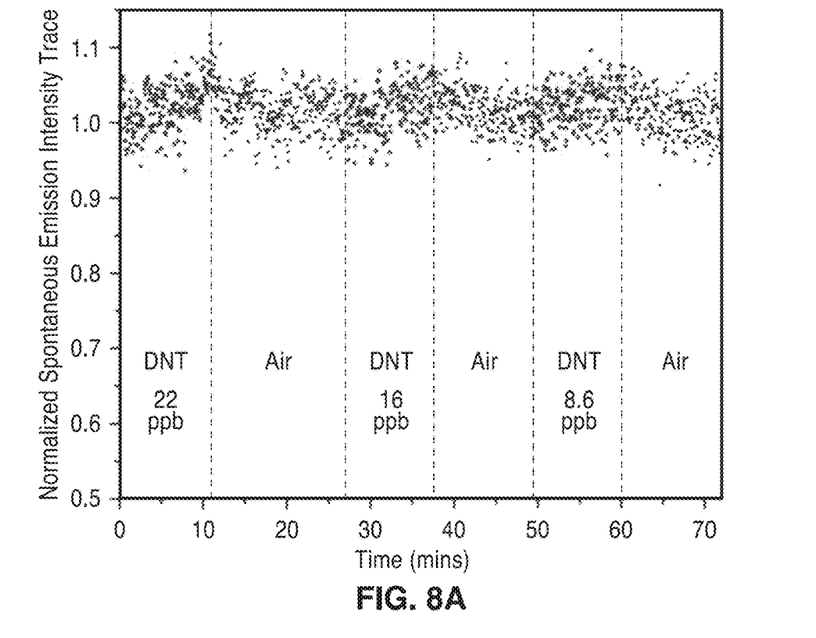
FIG. 8A shows a plot of continuous trace of spontaneous emission intensities at varied DNT vapor concentrations diluted by air.
Figure 8B:
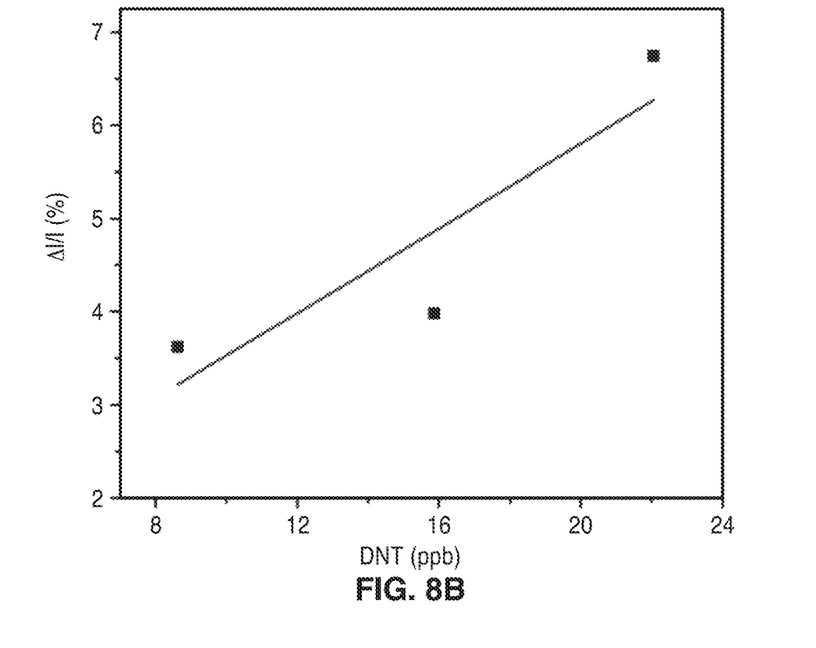
FIG. 8B shows a plot of calibration curves for DNT detection via spontaneous emission. The sensitivity and the detection limit are obtained to be ~0.23%/p.p.b. and ~14 p.p.b. respectively.
Figure 8C:
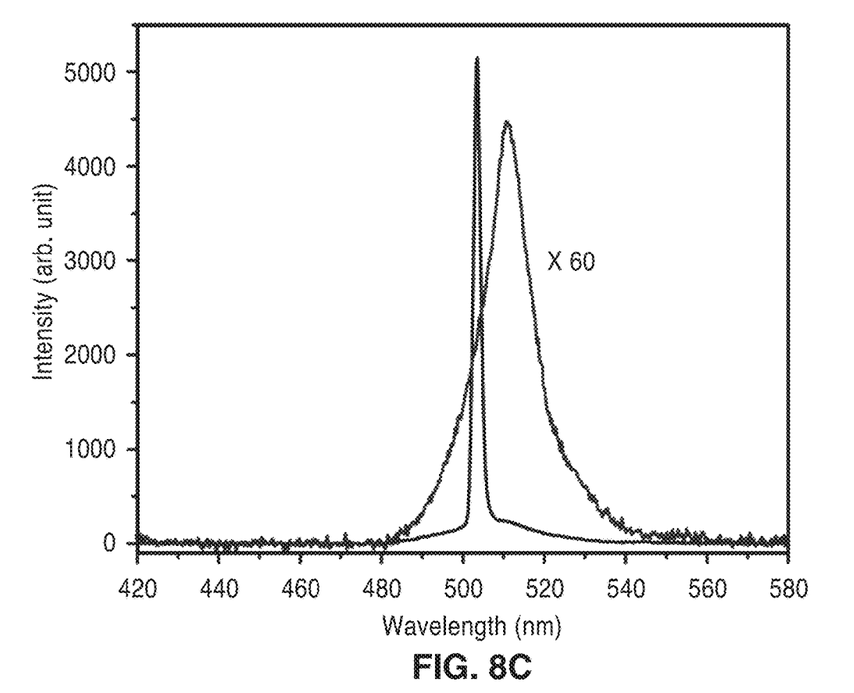
FIG. 8C shows a plot of spontaneous emission and lasing emission of the sensor device of the present description.

The sensitivity of the sensor 10 the lasing condition is significantly enhanced compared to that in the spontaneous emission condition. FIG. 8A shows the continuous trace of spontaneous emission intensities when DNT was delivered vapors at varied concentrations. FIG. 8B shows the calibration curves for DNT detection in the spontaneous emission condition. The sensitivity and the detection limit are obtained to be 0.23%/p.p.b. and 14 p.p.b. respectively. It can be seen that the sensitivity of lasing emission is ~5 times higher than that of spontaneous emission, and detection limit is ~21 times better. It is noted that the peak intensity of the lasing emission is about 60 times higher than that of the spontaneous emission (FIG. 8C). Accordingly, the sensitivity of lasing emission is ~300 times higher than that of spontaneous emission when $\Delta I$ is used as a direct measure of the signal.

In summary, an active plasmon sensor with sub-p.p.b. level explosive molecules detection was experimentally demonstrated. Furthermore, it was found that: (1) while solid state semiconductor simultaneously acted as optical gain and sensing medium in active plasmon sensors, the device 10 detected different explosive molecules with specific response depending on the molecules' electron deficiencies; (2) the sensitivity of lasing emission from calibration curve was ~300 times higher than that of spontaneous emission, because the lasing emission has much stronger intensity and higher slope efficiency; (3) directly monitoring lasing intensity had superior performance than monitoring wavelength shift due to the index change. The late one was hardly distinguishable in the ultra-trace detection. These results demonstrate the potential of actively excited surface plasmon for chemical sensing that could be important for security, defense and other applications.

The efficacy of the sensor was validated to detect explosives in air under normal conditions and achieve sub-ppb detection limit, the lowest limit reported so far for plasmonic sensors, for 2, 4-dinitrotoluene (DNT) and ammonium nitrate (AN). Selectivity between DNT, AN and nitrobenzene (NB) is on-par with other state-of-the art explosive detectors. Furthermore, the results show that monitoring the change of the lasing intensity is a method with superior performance than monitoring the wavelength shift, which is widely used in passive surface plasmon sensors. Thus, nanoscopic sensors in accordance with the present description, making use of plasmonic lasing, may provide an important tool in security screening and biomolecular diagnostics.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

From the description herein, it will be appreciated that that the present disclosure encompasses multiple embodiments which include, but are not limited to, the following:

1. An active plasmon sensor, comprising: a layer of crystalline semiconductor material; a layer of a metal material; and a layer of dielectric material between the layer of crystalline semiconductor material and the layer of metal material.

2. The sensor of any preceding embodiment, wherein the layer of crystalline semiconductor material comprises a single crystalline semiconductor CdS nano-slab.

3. The sensor of any preceding embodiment, wherein the layer of metal material comprises silver.

4. The sensor of any preceding embodiment, wherein the dielectric material comprises magnesium fluoride.

5. The sensor of any preceding embodiment, wherein the sensor is configured such that surface plasmons are actively excited within the semiconductor material.

6. The sensor of any preceding embodiment, wherein the surface plasmons localize an electromagnetic field at an interface between the metal material and the semiconductor material.

7. The sensor of any preceding embodiment, wherein the semiconductor material has an atomically smooth surface having a film roughness (RMS) measured by AFM less than 1 nm.

8. The sensor of any preceding embodiment wherein the semiconductor material simultaneously functions as a gain and nanoscale sensing medium in a lasing plasmon nano-cavity.

9. The sensor of any preceding embodiment, wherein the sensor is configured to detect an explosive material.

10. A method of detecting an analyte in a lasing plasmon nano-cavity, the method comprising: subjecting the plasmon nano-cavity to an analyte; the plasmon nano-cavity comprising a dielectric material disposed between a layer of crystalline semiconductor nano-slab sensing surface and a layer of a metal material; and monitoring a change of the lasing intensity of a lasing emission of the plasmon nano-cavity.

11. The method of any preceding embodiment, wherein monitoring a change of the lasing intensity comprises detecting a change in peak intensity of the lasing emission as a result of the analyte adsorbing on the sensing surface.

12. The method of any preceding embodiment, wherein the crystalline semiconductor nano-slab comprises a single crystalline semiconductor CdS nano-slab.

13. The method of any preceding embodiment, wherein the layer of metal material comprises silver.

14. The method of any preceding embodiment, wherein the dielectric material comprises magnesium fluoride.

15. The method of any preceding embodiment, wherein monitoring a change of the lasing intensity comprises actively exciting surface plasmons in the semiconductor material.

16. The method of any preceding embodiment, wherein the surface plasmons localize an electromagnetic field at an interface between the metal material and the nano-slab.

17. The method of any preceding embodiment, wherein the semiconductor material has an atomically smooth surface having a film roughness (RMS) measured by AFM less than 1 nm.

18. The method of any preceding embodiment, wherein the semiconductor material simultaneously functions as a gain and nanoscale sensing medium in a lasing plasmon nano-cavity.

19. The method of any preceding embodiment, wherein the analyte comprises an explosive material.

20. An active plasmon sensor, comprising: a layer of crystalline semiconductor material; a layer of a metal material; and a layer of dielectric material between the layer of crystalline semiconductor material and the layer of metal material; wherein the sensor is configured such that surface plasmons are actively excited within the semiconductor material; wherein, upon actively exciting the sensor, the surface plasmons localize an electromagnetic field at an interface between the metal material and the semiconductor material.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method of detecting an analyte in a lasing plasmon nano-cavity, the method comprising:
    subjecting the plasmon nano-cavity to an analyte;
    the plasmon nano-cavity comprising a dielectric material disposed between a layer of crystalline semiconductor nano-slab and a layer of a metallic material, the layer of crystalline semiconductor nano-slab having a sensing surface; and
    monitoring a change of the lasing intensity of a lasing emission of the plasmon nano-cavity.

2. The method of claim 1, wherein monitoring a change of the lasing intensity comprises detecting a change in peak intensity of the lasing emission as a result of the analyte adsorbing on the sensing surface.

3. The method of claim 1, wherein the crystalline semiconductor nano-slab comprises a single crystalline semiconductor CdS nano-slab.

4. The method of claim 1, wherein the layer of metallic material comprises silver.

5. The method of claim 1, wherein the dielectric material comprises magnesium fluoride.

6. The method of claim 1, wherein monitoring a change of the lasing intensity comprises actively exciting surface plasmons in the semiconductor material.

7. The method of claim 6, wherein the surface plasmons localize an electromagnetic field at an interface between the metallic material and the nano-slab.

8. The method of claim 1, wherein the semiconductor material has an atomically smooth surface having a film roughness (RMS) measured by AFM less than 1 nm.

9. The method of claim 1, wherein the semiconductor material simultaneously functions as a gain and nanoscale sensing medium in a lasing plasmon nano-cavity.

10. The method of claim 1, wherein the analyte comprises an explosive material.

11. The method of claim 1, wherein the dielectric layer separates the layer of crystalline semiconductor nano-slab from the layer of a metallic material.

12. The method of claim 1, wherein the sensing surface comprises a free surface opposite the layer of a metallic material from the dielectric layer.

* * * * *